US011471329B1

(12) United States Patent
Chin (10) Patent No.: US 11,471,329 B1
(45) Date of Patent: Oct. 18, 2022

(54) ASSEMBLED FULL-FACE MASK

(71) Applicant: ASWAN INTERNATIONAL CORP., Taipei (TW)

(72) Inventor: Meng-Hsien Chin, Taipei (TW)

(73) Assignee: ASWAN INTERNATIONAL CORP., Taipei (TW)

( * ) Notice: Subject to any disclaimer, the term of this patent is extended or adjusted under 35 U.S.C. 154(b) by 16 days.

(21) Appl. No.: 17/209,241

(22) Filed: Mar. 23, 2021

(51) Int. Cl.
*A61F 9/02* (2006.01)
*A42B 3/20* (2006.01)
*A63B 71/10* (2006.01)

(52) U.S. Cl.
CPC ............... *A61F 9/029* (2013.01); *A42B 3/20* (2013.01); *A61F 9/022* (2013.01); *A61F 9/025* (2013.01); *A63B 71/10* (2013.01)

(58) Field of Classification Search
CPC . A42B 3/20; A61F 9/022; A61F 9/025; A61F 9/029; A63B 71/10
See application file for complete search history.

(56) References Cited

U.S. PATENT DOCUMENTS

| | | | | |
|---|---|---|---|---|
| 3,298,031 A * | 1/1967 | Morgan | ........ | A61F 9/029 2/427 |
| 3,528,415 A * | 9/1970 | Malmin | ........ | A41D 13/11 128/202.13 |
| 4,250,577 A * | 2/1981 | Smith | ........ | A62B 18/084 2/427 |
| 4,653,124 A * | 3/1987 | McNeal | ........ | A61F 9/029 2/427 |
| 5,107,543 A * | 4/1992 | Hansen | ........ | A41D 13/1184 2/427 |
| 5,603,117 A * | 2/1997 | Hudner, Jr. | ........ | A42B 3/127 2/6.6 |
| 6,178,561 B1 * | 1/2001 | Cheng | ........ | A61F 9/025 2/13 |
| 6,357,053 B1 * | 3/2002 | Wang-Lee | ........ | A61F 9/025 2/431 |
| 6,363,528 B1 * | 4/2002 | Cyr | ........ | A42B 3/20 2/9 |
| 6,381,749 B1 * | 5/2002 | Cyr | ........ | A42B 3/20 2/427 |
| 6,804,829 B2 * | 10/2004 | Crye | ........ | A42B 3/12 2/9 |

(Continued)

FOREIGN PATENT DOCUMENTS

AU       2012238227 A1 *  5/2013  ............ A61F 9/029

*Primary Examiner* — F Griffin Hall
(74) *Attorney, Agent, or Firm* — Li & Cai Intellectual Property Office (57) ABSTRACT

An assembled full-face mask includes a goggle, an outer lens, and a mask shell. The outer lens includes a sheet and a pivotal frame that is connected to the sheet. The pivotal frame is assembled to the goggle, and the outer lens is rotatable relative to the goggle along a first axis. The mask shell includes two connection rods assembled to the goggle and a shell body that is connected to the two connection rods. The mask shell is rotatable relative to the goggle along a second axis that is parallel to and spaced apart from the first axis. When one of the outer lens and the mask shell is rotated relative to the goggle by a first angle, another one of the outer lens and the mask shell is rotatable relative to the goggle by a second angle that is less than the first angle.

17 Claims, 11 Drawing Sheets

(56) References Cited

U.S. PATENT DOCUMENTS

| | | | | |
|---|---|---|---|---|
| 6,886,183 B2* | 5/2005 | DeHaan | A42B 3/20 | 2/6.7 |
| 6,948,813 B2* | 9/2005 | Parks | A61F 9/025 | 351/158 |
| 6,957,447 B1* | 10/2005 | Broersma | A63B 71/10 | 2/427 |
| 7,003,802 B2* | 2/2006 | Broersma | A63B 71/10 | 2/427 |
| 7,058,991 B2* | 6/2006 | Hartman | A61F 9/025 | 2/437 |
| 7,168,095 B2* | 1/2007 | Wright | A41D 13/11 | 2/430 |
| 7,320,144 B2* | 1/2008 | Katz | A42B 3/185 | 2/9 |
| 7,681,257 B1* | 3/2010 | Broersma | A42B 3/20 | 2/431 |
| RE41,834 E* | 10/2010 | Parks | A61F 9/025 | 351/158 |
| 7,895,680 B2* | 3/2011 | Anderson | A42B 3/18 | 2/427 |
| 8,104,095 B2* | 1/2012 | Cyr | A41D 13/1184 | 2/9 |
| 8,166,578 B2* | 5/2012 | Tan | A61F 9/025 | 2/427 |
| 8,225,431 B2* | 7/2012 | Cyr | A42B 3/22 | 2/6.3 |
| 8,549,672 B2* | 10/2013 | Stevens | A61F 9/029 | 2/427 |
| 10,736,782 B2* | 8/2020 | Hofer Kraner | A61F 9/067 | |
| 2004/0111779 A1* | 6/2004 | Gagnon | A42B 3/20 | 2/9 |
| 2006/0085883 A1* | 4/2006 | Tan | A41D 13/1107 | 2/427 |
| 2006/0090234 A1* | 5/2006 | Cyr | A63B 71/10 | 2/9 |
| 2006/0272067 A1* | 12/2006 | Gagnon | A41D 13/11 | 2/9 |
| 2007/0050895 A1* | 3/2007 | Broersma | A42B 3/20 | 2/426 |
| 2007/0186324 A1* | 8/2007 | Sheldon | A42B 3/20 | 2/9 |
| 2007/0192946 A1* | 8/2007 | Wright | A61F 9/045 | 2/424 |
| 2008/0127400 A1* | 6/2008 | Dupuis | F41H 1/02 | 2/9 |
| 2009/0113590 A1* | 5/2009 | Lian | A63B 71/10 | 2/9 |
| 2009/0113607 A1* | 5/2009 | Lian | A41D 13/1184 | 2/427 |
| 2014/0196199 A1* | 7/2014 | Huffman | A42B 3/20 | 2/421 |
| 2016/0029734 A1* | 2/2016 | Kurpjuweit | A42B 3/205 | 2/427 |
| 2020/0368068 A1* | 11/2020 | Wu | A41D 13/1184 | |

* cited by examiner

ASSEMBLED FULL-FACE MASK

FIELD OF THE DISCLOSURE

The present disclosure relates to a mask, and more particularly to an assembled full-face mask.

BACKGROUND OF THE DISCLOSURE

A conventional full-face mask for covering the entire face of a user is integrally formed as a single one-piece structure, which results in a lot of inconvenience for the user. For example, when the user needs to talk on the phone, the conventional full-face mask has to be completely removed.

SUMMARY OF THE DISCLOSURE

In response to the above-referenced technical inadequacy, the present disclosure provides an assembled full-face mask to effectively improve on the issues associated with conventional full-face masks.

In one aspect, the present disclosure provides an assembled full-face mask, which includes a goggle, an outer lens, and a mask shell. The goggle includes a lens frame, a pivotal seat, and a lens. The lens frame is in an annular shape and has a top portion, two lateral portions, a bottom portion, and two pivotal portions that are respectively formed on the two lateral portions. The pivotal seat is disposed on the top portion. The lens is assembled to the lens frame and is arranged in a space that is surroundingly defined by the top portion, the two lateral portions, and the bottom portion. The outer lens includes a sheet and a pivotal frame that is connected to the sheet. The pivotal frame is assembled to the pivotal seat, the sheet covers the lens, and the outer lens is rotatable relative to the goggle along a first axis. The mask shell includes two connection rods and a shell body. The two connection rods are respectively assembled to the two pivotal portions. The shell body is connected to the two connection rods. The mask shell is rotatable relative to the goggle along a second axis that is parallel to and spaced apart from the first axis. When one of the outer lens and the mask shell is rotated relative to the goggle by a first angle, another one of the outer lens and the mask shell is rotatable relative to the goggle by a second angle that is less than the first angle.

In another aspect, the present disclosure provides an assembled full-face mask, which includes a goggle, an outer lens, and a mask shell. The outer lens includes a sheet and a pivotal frame that is connected to the sheet. The pivotal frame is assembled to the goggle, and the outer lens is rotatable relative to the goggle along a first axis. The mask shell includes two connection rods and a shell body. The two connection rods are assembled to the goggle. The shell body is connected to the two connection rods. The mask shell is rotatable relative to the goggle along a second axis that is parallel to and spaced apart from the first axis. When one of the outer lens and the mask shell is rotated relative to the goggle by a first angle, another one of the outer lens and the mask shell is rotatable relative to the goggle by a second angle that is less than the first angle.

Therefore, any one of the outer lens and the mask shell of the assembled full-face mask in the present disclosure can be independently rotatable relative to the goggle by the structural design of the goggle in cooperation with the outer lens and the mask shell, thereby providing convenience in use of the assembled full-face mask.

These and other aspects of the present disclosure will become apparent from the following description of the embodiment taken in conjunction with the following drawings and their captions, although variations and modifications therein may be affected without departing from the spirit and scope of the novel concepts of the disclosure.

BRIEF DESCRIPTION OF THE DRAWINGS

The described embodiments may be better understood by reference to the following description and the accompanying drawings, in which.

DETAILED DESCRIPTION OF THE EXEMPLARY EMBODIMENTS

The present disclosure is more particularly described in the following examples that are intended as illustrative only since numerous modifications and variations therein will be apparent to those skilled in the art. Like numbers in the drawings indicate like components throughout the views. As used in the description herein and throughout the claims that follow, unless the context clearly dictates otherwise, the meaning of "a", "an", and "the" includes plural reference, and the meaning of "in" includes "in" and "on". Titles or subtitles can be used herein for the convenience of a reader, which shall have no influence on the scope of the present disclosure.

The terms used herein generally have their ordinary meanings in the art. In the case of conflict, the present document, including any definitions given herein, will prevail. The same thing can be expressed in more than one way. Alternative language and synonyms can be used for any term(s) discussed herein, and no special significance is to be placed upon whether a term is elaborated or discussed herein. A recital of one or more synonyms does not exclude the use of other synonyms. The use of examples anywhere in this specification including examples of any terms is illustrative only, and in no way limits the scope and meaning of the present disclosure or of any exemplified term. Likewise, the present disclosure is not limited to various embodiments given herein. Numbering terms such as "first", "second" or "third" can be used to describe various components, signals or the like, which are for distinguishing one component/signal from another one only, and are not intended to, nor should be construed to impose any substantive limitations on the components, signals or the like.

Figure 1:
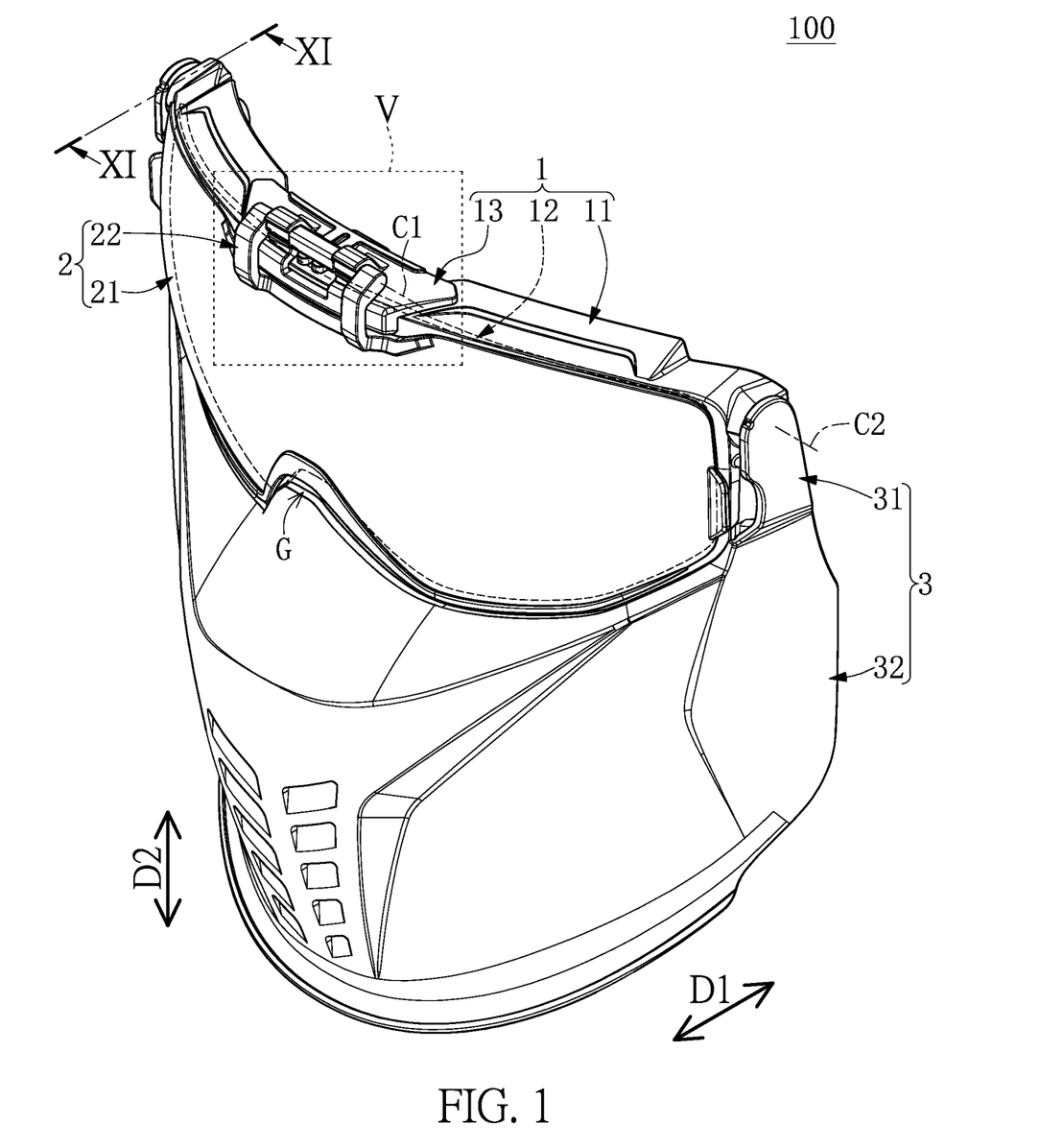
FIG. 1 is a perspective view of an assembled full-face mask according to an embodiment of the present disclosure.
Figure 2:
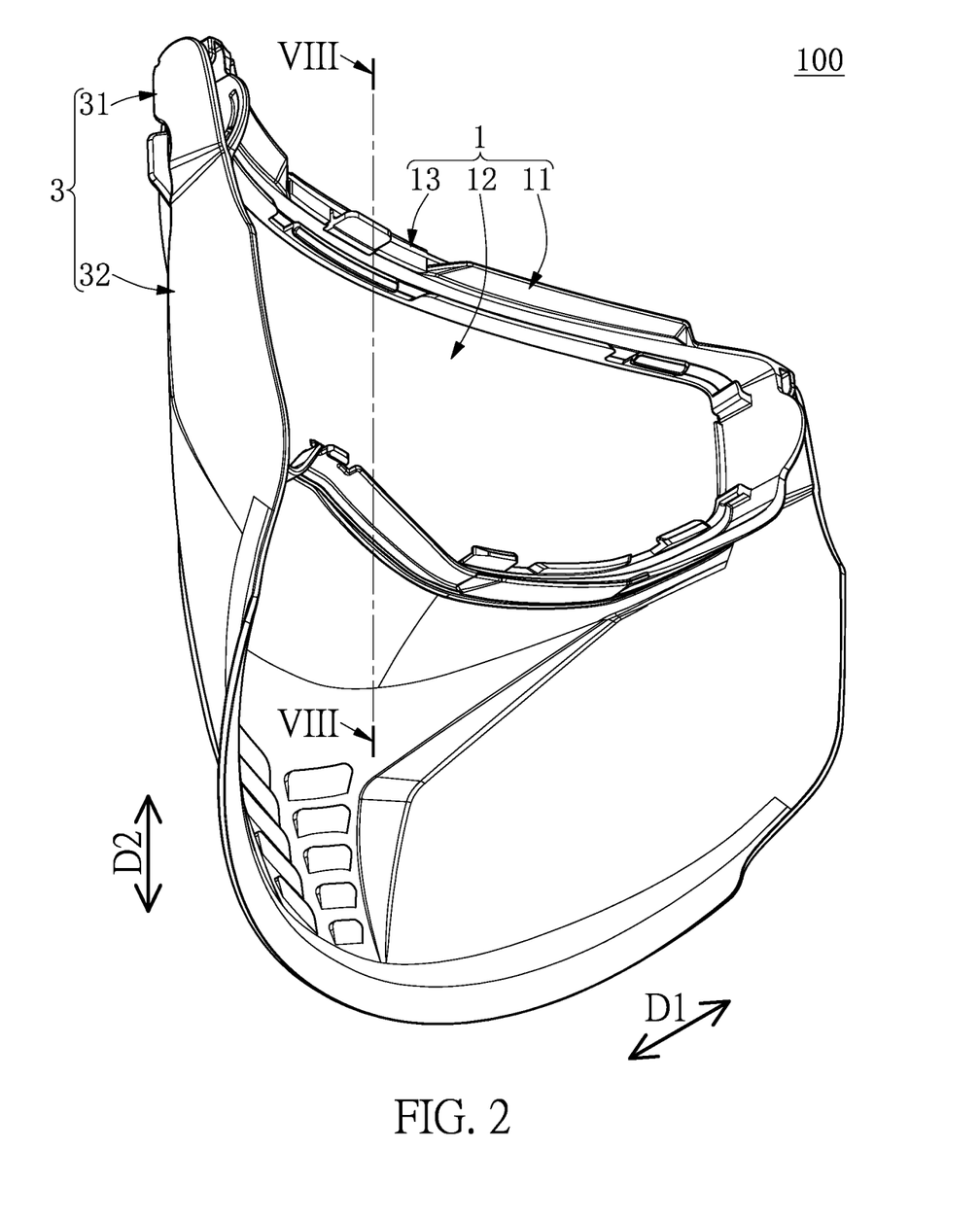
FIG. 2 is a perspective view showing the assembled full-face mask of FIG. 1 from another angle of view.
Figure 3:
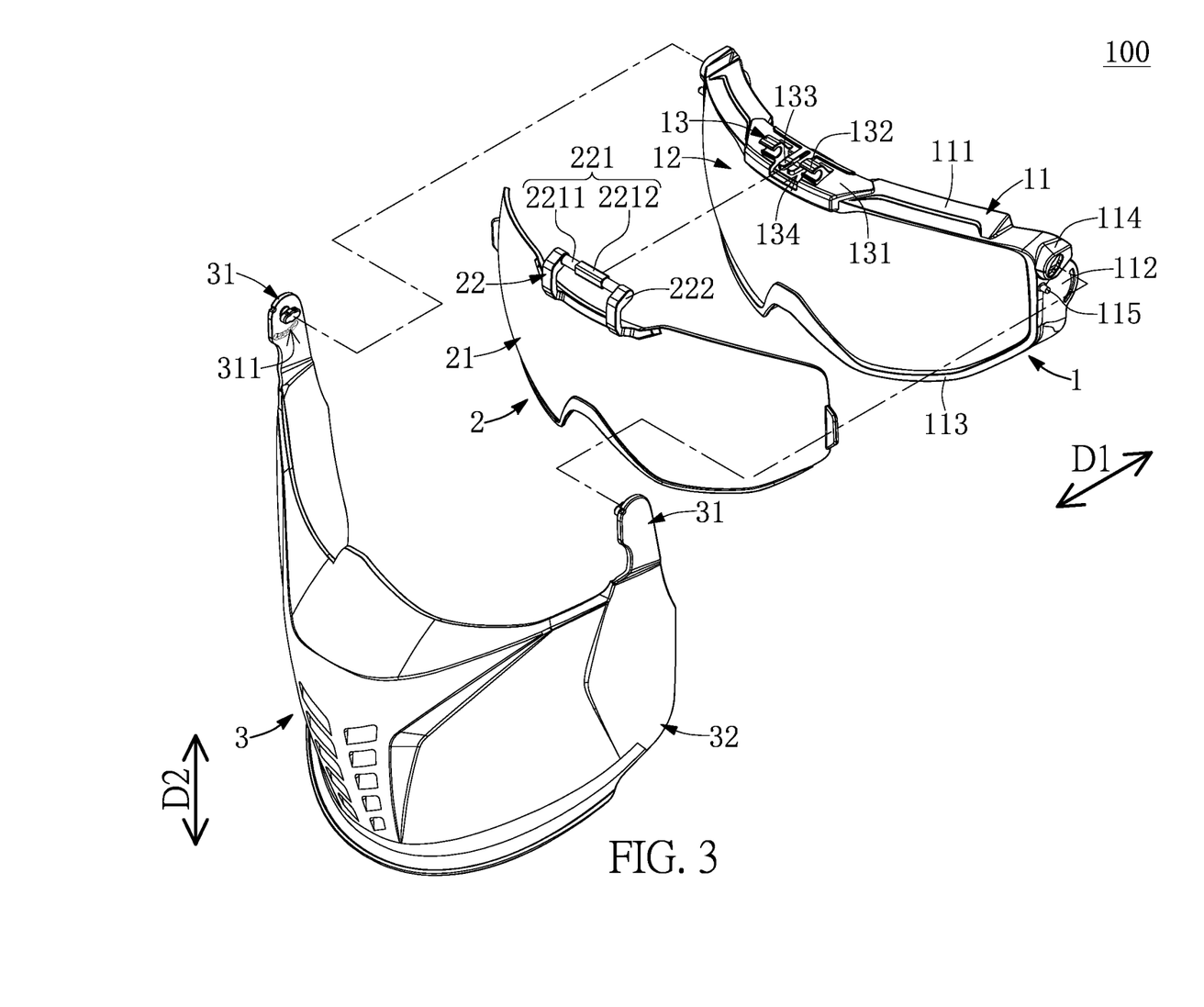
FIG. 3 is an exploded view of FIG. 1.

Referring to FIG. 1 to FIG. 11, an embodiment of the present disclosure provides an assembled full-face mask 100 for substantially covering the entire face of a user. As shown in FIG. 1 to FIG. 3, the assembled full-face mask 100 includes a goggle 1, an outer lens 2 pivotally connected to the goggle 1 along a first axis C1, and a mask shell 3 that is pivotally connected to the goggle 1 along a second axis C2. The first axis C1 is parallel to and spaced apart from the second axis C2, and any one of the outer lens 2 and the mask shell 3 is independently rotatable relative to the goggle 1, thereby providing convenience of using the assembled full-face mask 100.

Moreover, in order to clearly describe the structure of the assembled full-face mask 100, the assembled full-face mask 100 defines a bisecting plane P perpendicular to the first axis C1 and the second axis C2, and the bisecting plane P can be defined by a first direction D1 and a second direction D2 that is perpendicular to the first direction D1. The first direction D1 in the present embodiment is parallel to a forward viewing direction of the goggle 1. In other words, the assembled full-face mask 100 in the present embodiment is a mirror-symmetrical structure with respect to the bisecting plane P.

Figure 4:
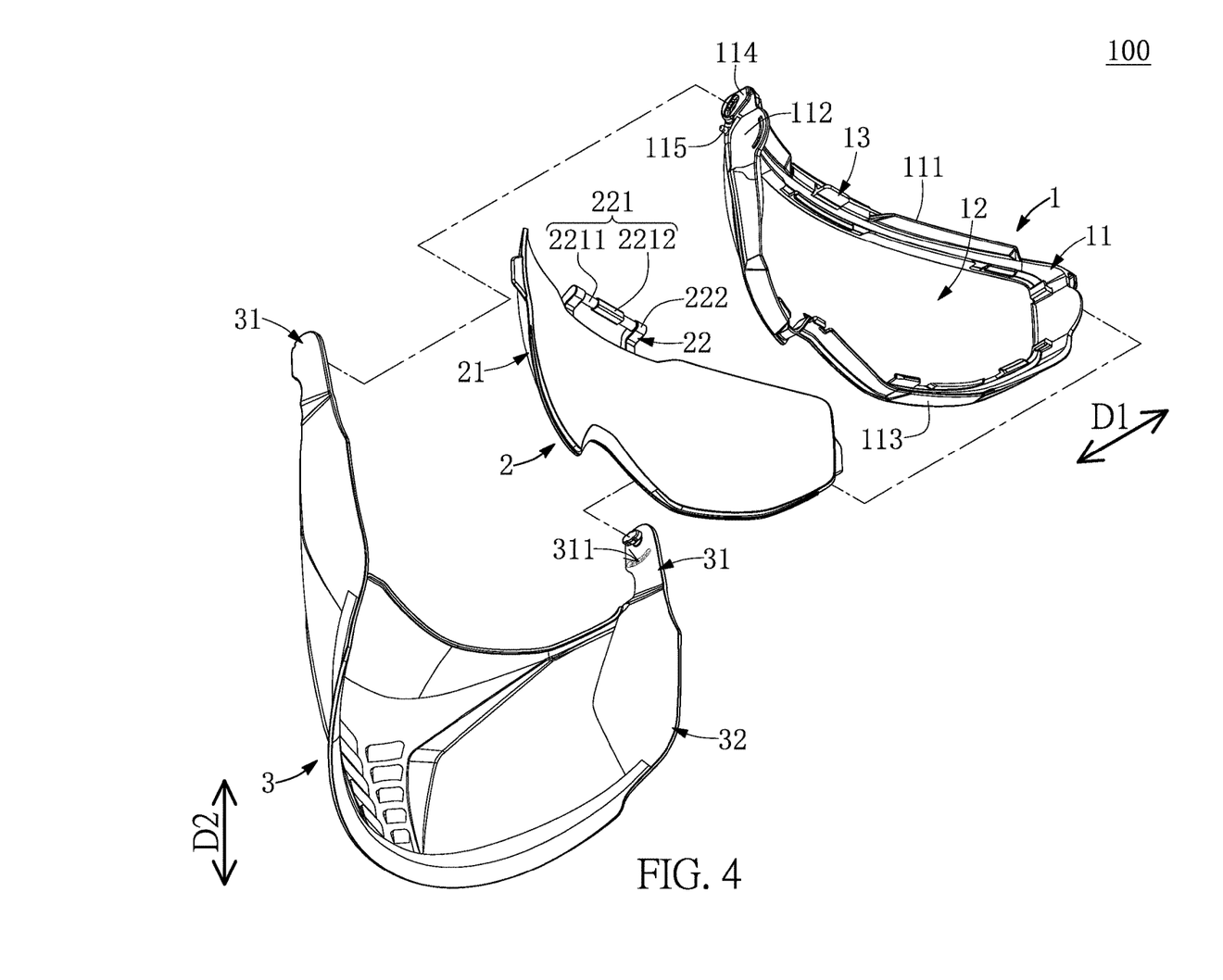
FIG. 4 is an exploded view of FIG. 2.
Figure 5:
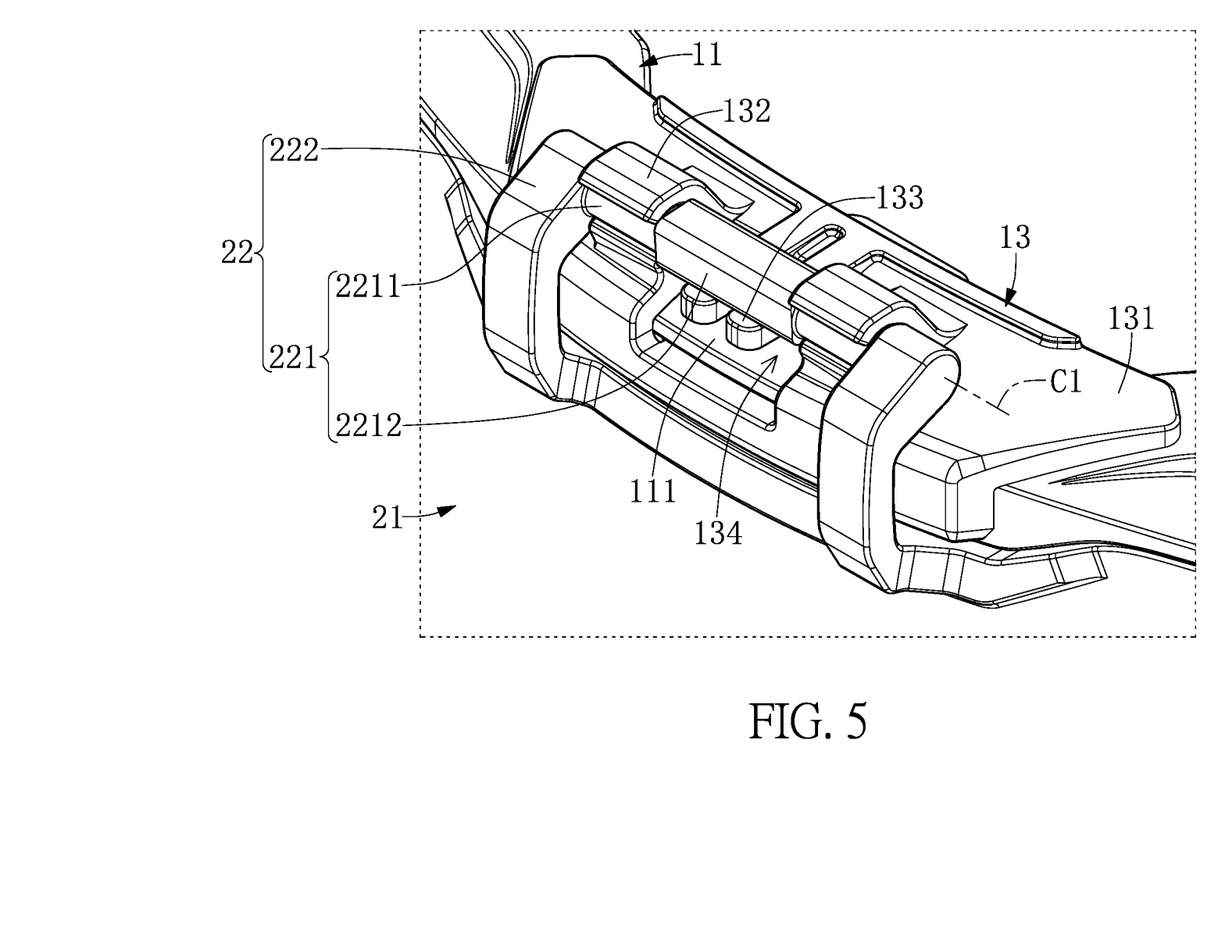
FIG. 5 shows an enlarged view of part V of FIG. 1.

As shown in FIG. 3 to FIG. 5, the goggle 1 in the present embodiment includes a lens frame 11, a lens 12 fixed to the lens frame 11, and a pivotal seat 13 that is detachably assembled to the lens frame 11, but the present disclosure is not limited thereto. For example, in other embodiments of the present disclosure not shown in the drawings, the goggle 1 can be other structures (e.g., the lens frame 11 and the pivotal seat 13 are integrally formed as a single one-piece structure); or, the goggle 1 can be formed by adding other components.

The lens frame 11 is in an annular shape and includes a top portion 111, two lateral portions 112, a bottom portion 113, two pivotal portions 114 respectively formed on the two lateral portions 112, and two positioning columns 115 that are respectively formed on the two lateral portions 112. The top portion 111 and the two lateral portions 112 are connected to each other so as to jointly form in a substantial U-shape, the bottom portion 113 is in a substantial W-shape, and two distal ends of the bottom portion 113 are respectively connected to the two lateral portions 112. Moreover, the lens 12 is assembled to the lens frame 11, and is arranged in a space that is surroundingly defined by the top portion 111, the two lateral portions 112, and the bottom portion 113.

Figure 6:
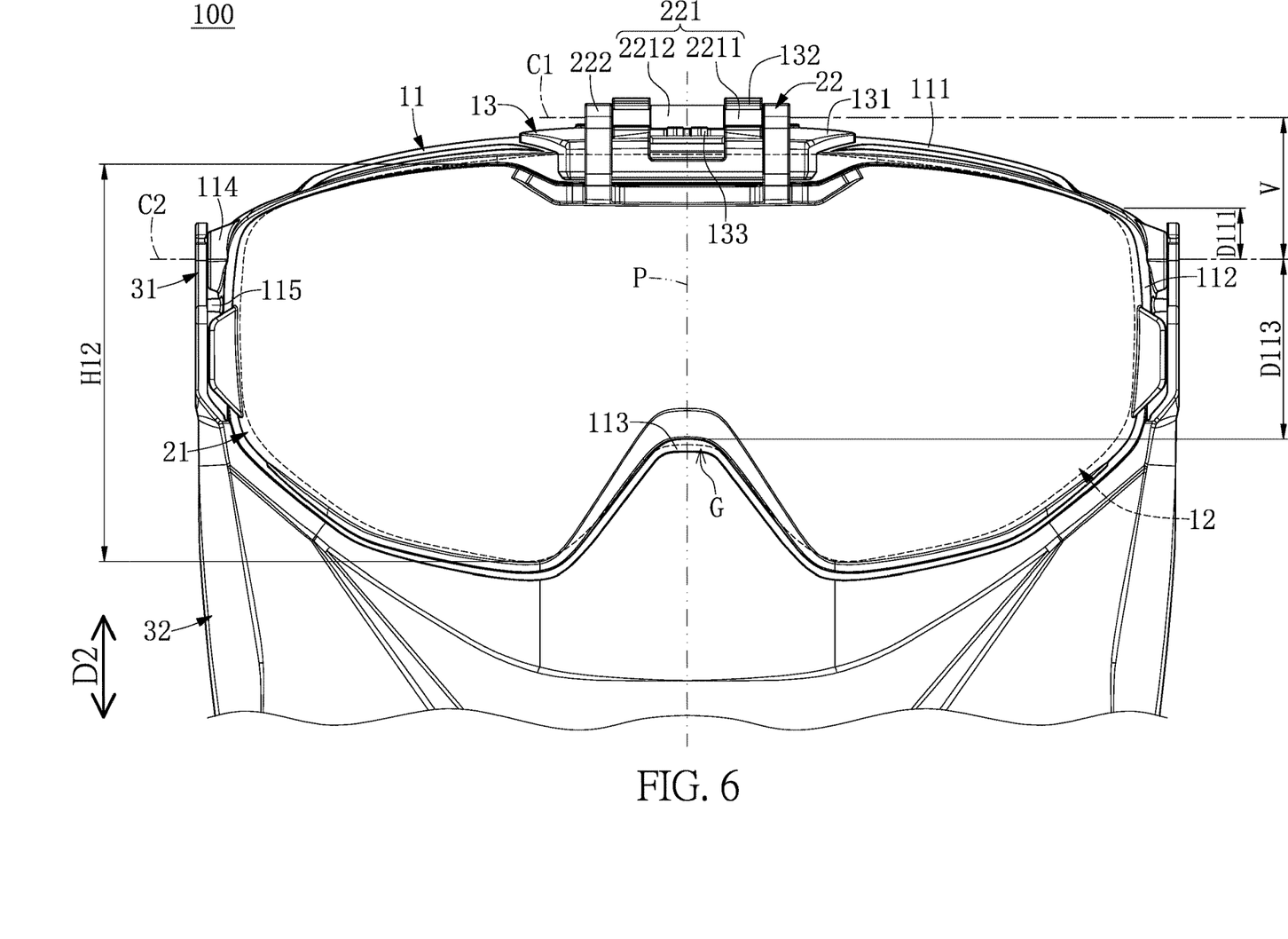
FIG. 6 is a partial front view of FIG. 1.

Specifically, the two pivotal portions 114 are arranged adjacent to the top portion 111, and the two pivotal portions 114 can jointly define the second axis C2, but the present disclosure is not limited thereto. In other words, a distance D113 between the second axis C2 and the bottom portion 113 is at least four times of a distance D111 between the second axis C2 and the top portion 111 (as shown in FIG. 6). The two positioning columns 115 are respectively arranged adjacent to the two pivotal portions 114, and are respectively located under the two pivotal portions 114. In the present embodiment, any one of the two positioning columns 115 is in a cylindrical shape, and a height of any one of the two positioning columns 115 is slightly larger than a height of the pivotal portion 114 adjacent thereto. The two positioning columns 115 are arranged adjacent to the lens 12.

The pivotal seat 13 is disposed on the top portion 111 of the lens frame 11, and is preferably detachably assembled to (e.g., buckled with) a center region of the top portion 111. In the present embodiment, the pivotal seat 13 is integrally formed as a single one-piece structure, and includes a carrier 131 assembled to the top portion 111, two buckling portions 132 connected to the carrier 131, and two limiting cantilevers 133 that are connected to the carrier 131.

The pivotal seat 13 (or the two buckling portions 132) in the present embodiment can define the first axis C1, but the present disclosure is not limited thereto. The carrier 131 of the pivotal seat 13 has a hollow region 134 between the two buckling portions 132, and the two limiting cantilevers 133 are substantially arranged between the two buckling portions 132 and are arranged in the hollow region 134, so that any one of the two limiting cantilevers 133 in the hollow region 134 is elastically swingable toward the top portion 111.

Specifically, as shown in FIG. 6, on the bisecting plane P, the first axis C1 and the second axis C2 are spaced apart from each other along the first direction D1 by a longitudinal distance V. Moreover, a lens projection area defined by orthogonally projecting the lens 12 onto the bisecting plane P has a height H12 in the second direction D2, and the longitudinal distance V is 30% to 40% of the height H12.

Figure 7:
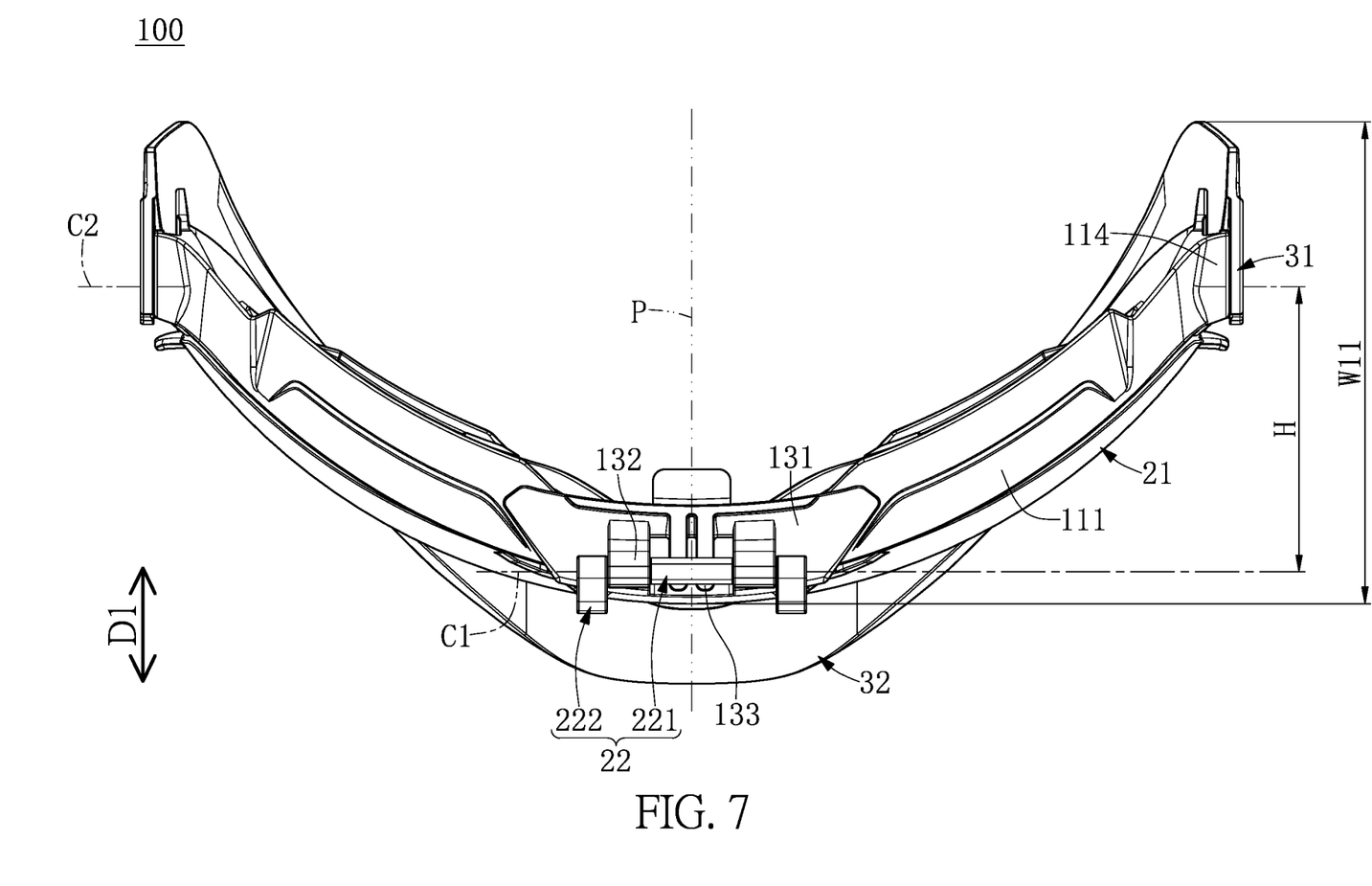
FIG. 7 is a top view of FIG. 1.

As shown in FIG. 7, on the bisecting plane P, the first axis C1 and the second axis C2 are spaced apart from each other along the first direction D1 by a transverse distance H. Moreover, a frame projection area defined by orthogonally projecting the lens frame 11 onto the bisecting plane P has a width W11 in the second direction D2, and the transverse distance H is equal to or less than the width W11.

It should be noted that a quantity of the limiting cantilevers 133 of the pivotal seat 13 is two, but the present disclosure is not limited thereto. For example, in other embodiments of the present disclosure not shown in the drawings, a quantity of the limiting cantilever 133 of the pivotal seat 13 can be at least one.

As shown in FIG. 3 to FIG. 5, the outer lens 2 in the present embodiment is integrally formed as a single one-piece structure, and includes a sheet 21 and a pivotal frame 22 that is connected to a top edge of the sheet 21. The sheet 21 of the outer lens 2 in the present embodiment is a filter, but the present disclosure is not limited thereto. For example, in other embodiments of the present disclosure not shown in the drawings, the sheet 21 can be a protective sheet having a hardness higher than that of the lens 12.

The pivotal frame 22 is assembled to the pivotal seat 13, so that the outer lens 2 is rotatable relative to the goggle 1 along the first axis C1, and the sheet 21 covers the lens 12. In the present embodiment, the shape of the sheet 21 is substantially identical to the shape of the lens 12, so that the sheet 21 can cover an entirety of the lens 12, but the present disclosure is not limited thereto. For example, in other embodiments of the present disclosure not shown in the drawings, the sheet 21 can cover a portion of the lens 12.

Moreover, the pivotal frame 22 includes a rotation shaft 221 arranged along the first axis C1 and two connection bridges 222 that are connected to the rotation shaft 221 and the sheet 21. A central axis of the rotation shaft 221 is overlapped with the first axis C1. A shaft projection area (as shown in FIG. 7) defined by orthogonally projecting the rotation shaft 221 onto the top portion 111 is preferably located at the center region of the top portion 111. Any one of the two connection bridges 222 in the present embodiment is connected to an end of the rotation shaft 221 and a top edge of the sheet 21 by straddling the carrier 131.

Specifically, the rotation shaft 221 includes two circular segments 2211 and a non-circular segment 2212 that is arranged between the two circular segments 2211. In other words, two ends of any one of the two circular segments 2211 are respectively connected to one of the two connection bridges 222 and the non-circular segment 2212. In the present embodiment, the circular segment 2211 has a circular cross section perpendicular to the first axis C1, and the non-circular segment 2212 has a non-circular cross section (e.g., a polygonal cross section) perpendicular to the first axis C1.

The two circular segments 2211 are rotatably assembled to the pivotal seat 13, and the non-circular segment 2212 abuts against and is retained by the pivotal seat 13 so as to fix the outer lens 2 at different positions when the outer lens 2 is rotated relative to the goggle 1. In the present embodiment, the two circular segments 2211 are respectively buckled into the two buckling portions 132, and the non-circular segment 2212 abuts against and is retained by the two limiting cantilevers 133, so that the two limiting cantilevers 133 are configured to provide a reaction force to the non-circular segment 2212.

Figure 8:
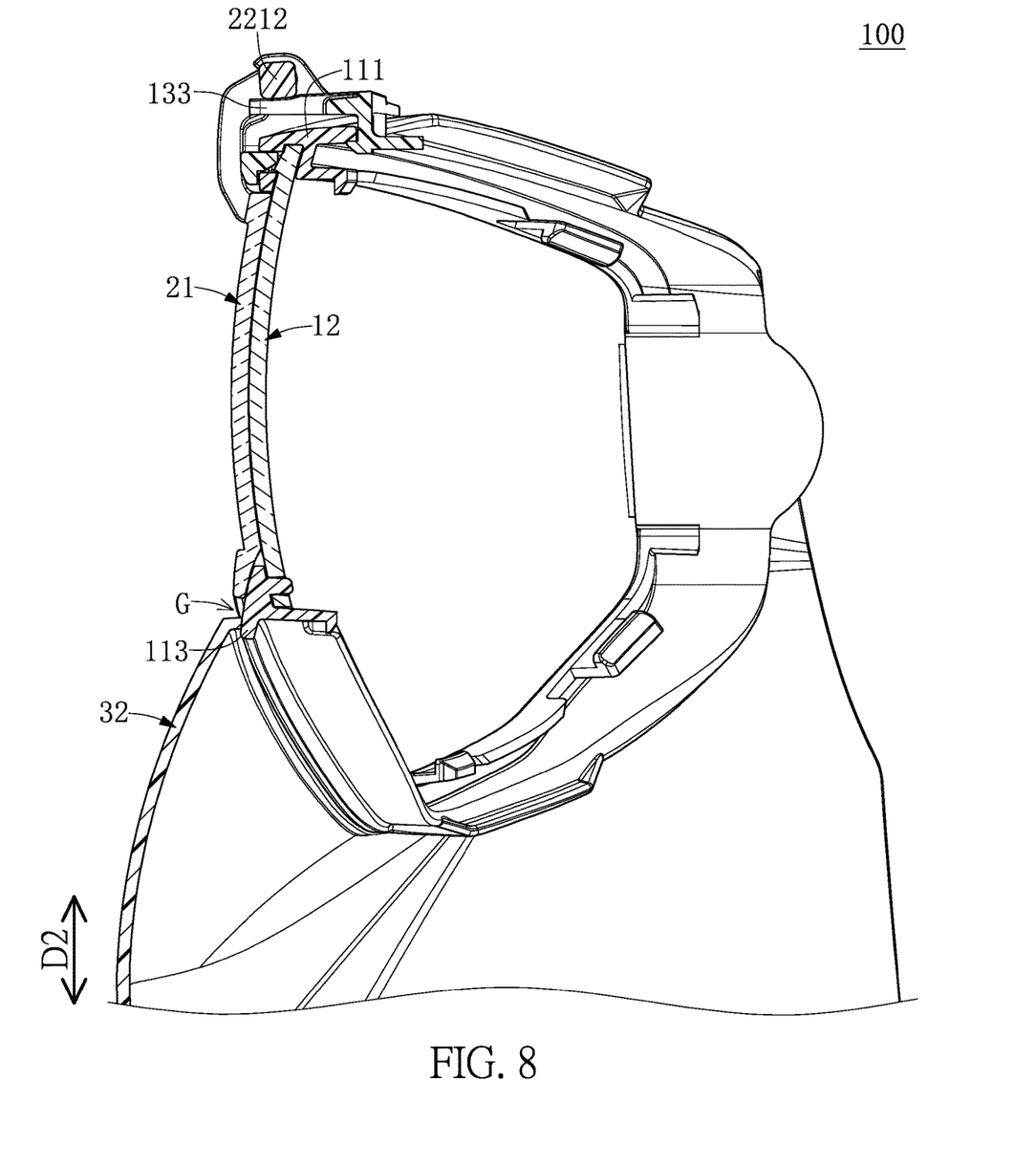
FIG. 8 is a cross-sectional view taken along line VIII-VIII of FIG. 2.

As shown in FIG. 3, FIG. 4, and FIG. 8, the mask shell 3 is integrally formed as a single one-piece structure, and includes two connection rods 31 and a shell body 32 that is connected to the two connection rods 31. The two connection rods 31 are respectively assembled to the two pivotal portions 114 (e.g., each of the two connection rods 31 is detachably assembled to the corresponding pivotal portion 114), so that the mask shell 3 is rotatable relative to the goggle 1 along the second axis C2. Specifically, a top edge of the shell body 32 and a bottom edge of the sheet 21 correspond in shape to each other and are spaced apart from each other so as to form an elongated gap G therebetween. Moreover, the top edge of the shell body 32 and the bottom edge of the sheet 21 can contact with an outer surface of the bottom portion 113 of the lens frame 11.

Figure 9:
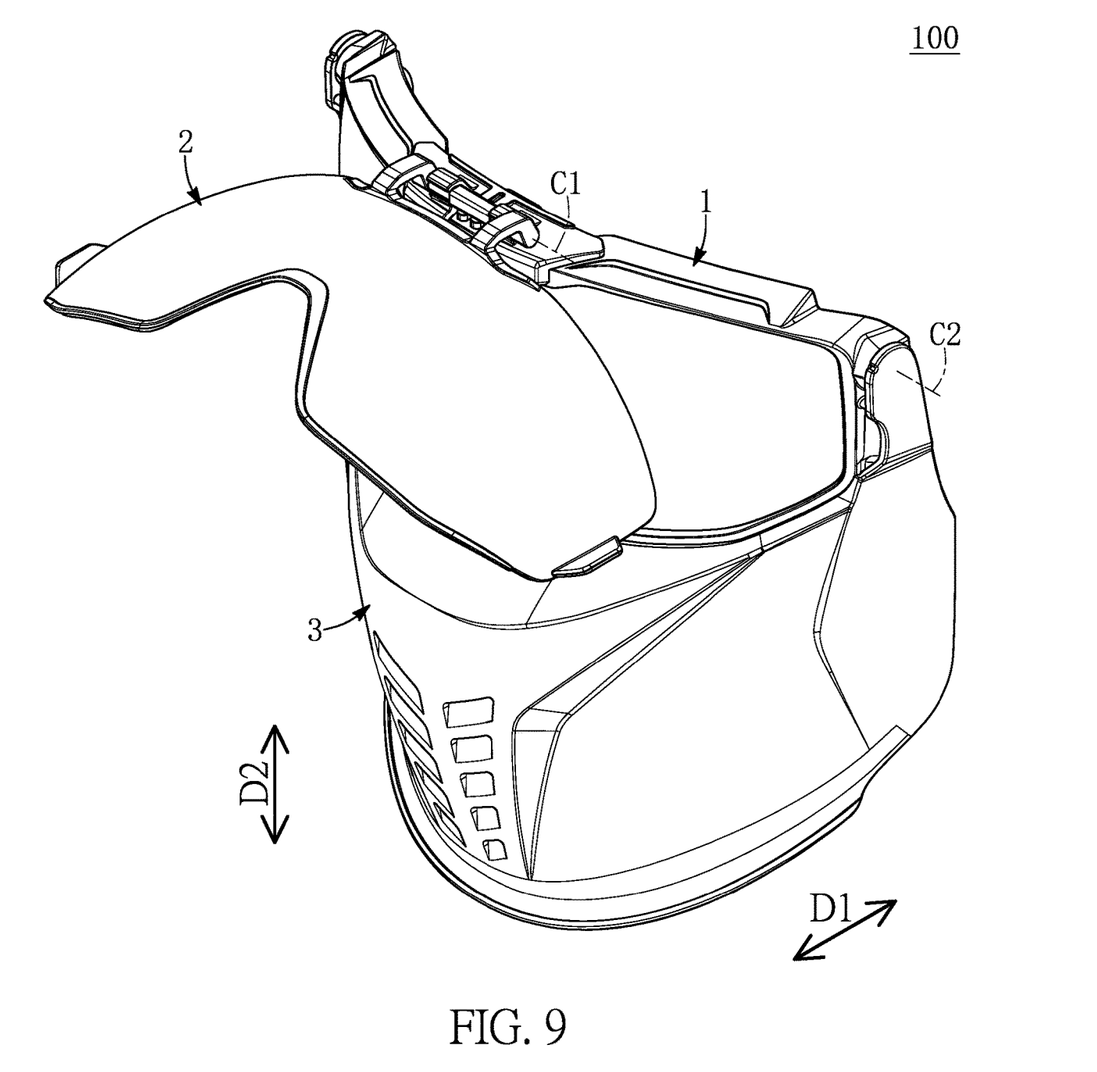
FIG. 9 is a perspective view showing the assembled full-face mask of FIG. 1, when an outer lens is rotated relative to a goggle.
Figure 10:
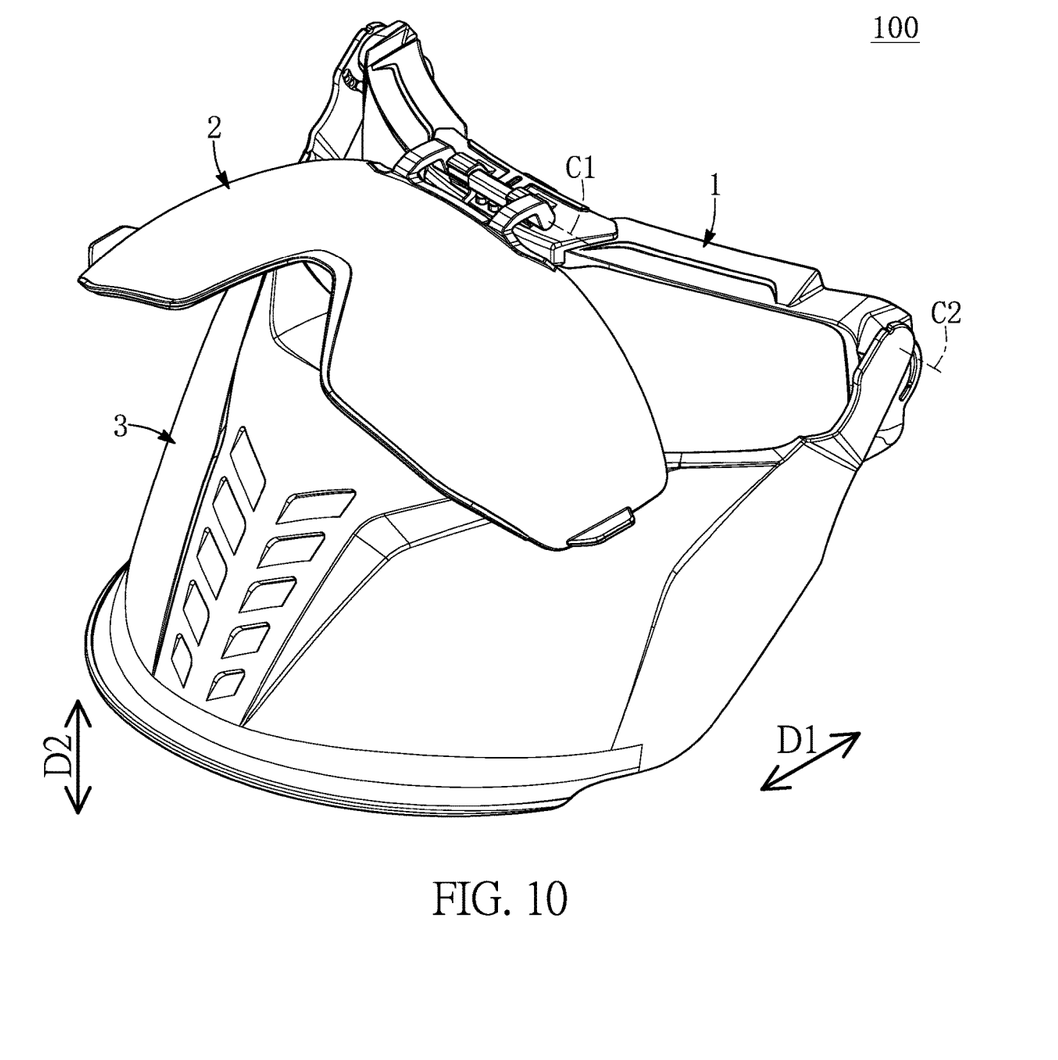
FIG. 10 is a perspective view showing the assembled full-face mask of FIG. 1 when the outer lens and a mask shell are rotated relative to the goggle.

As shown in FIG. 9 and FIG. 10, when one of the outer lens 2 and the mask shell 3 is rotated relative to the goggle 1 by a first angle, another one of the outer lens 2 and the mask shell 3 is rotatable relative to the goggle 1 by a second angle that is less than the first angle. In the present embodiment, a difference between the first angle and the second angle is within a range from 15 degrees to 35 degrees.

For example, when the assembled full-face mask 100 has the difference of 35 degrees and the outer lens 2 is rotated relative to the goggle 1 at 90 degrees (i.e., the first angle), the mask shell 3 can be rotated relative to the goggle 1 by an angle (i.e., the second angle) less than 55 degrees.

Figure 11:
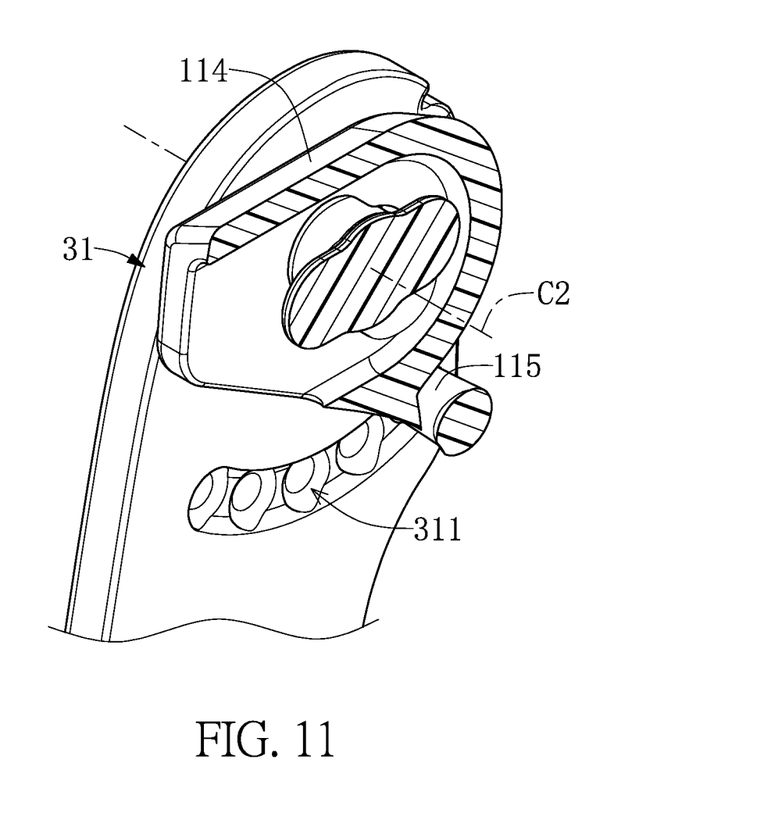
FIG. 11 is a cross-sectional view taken along line XI-XI of FIG. 1.

In addition, as shown in FIG. 3, FIG. 4, and FIG. 11, the two positioning columns 115 of the assembled full-face mask 100 respectively abut against and are retained by the two connection rods 31 so as to fix the mask shell 3 at different positions when the mask shell 3 is rotated relative to the goggle 1.

Specifically, each of the two connection rods 31 has a plurality of engaging slots 311. Each of the engaging slots 311 is spaced apart from the second axis C2 by a same distance that is equal to a distance between the corresponding positioning column 115 and the second axis C2, so that any one of the two positioning columns 115 can be selectively engaged with one of the engaging slots 311 of the corresponding connection rod 31. In any one of the two connection rods 31 of the present embodiment, the engaging slots 311 jointly define a central angle by taking the second axis C2 as a center of circle, and the central angle is within a range from 45 degrees to 70 degrees.

Beneficial Effects of the Embodiment

In conclusion, any one of the outer lens and the mask shell of the assembled full-face mask in the present disclosure can be independently rotatable relative to the goggle by the structural design of the goggle in cooperation with the outer lens and the mask shell, thereby providing convenience of using the assembled full-face mask.

Moreover, the goggle of the assembled full-face mask of the present disclosure can be in cooperation with the outer lens by detailed structural design thereof (e.g., the non-circular segment abuts against and is retained by the pivotal seat so as to fix the outer lens at different positions when the outer lens is rotated relative to the goggle; or, the non-circular segment abuts against and is retained by the limiting cantilever, so that the limiting cantilever is configured to provide a reaction force to the non-circular segment), thereby further increasing the convenience of using the outer lens of the assembled full-face mask.

In addition, the goggle of the assembled full-face mask of the present disclosure can be in cooperation with the mask shell by detailed structural design thereof (e.g., the two positioning columns respectively abut against and are retained by the two connection rods so as to fix the mask shell at different positions when the mask shell is rotated relative to the goggle; or, any one of the two positioning columns is selectively engaged with one of the engaging slots of the corresponding connection rod), thereby further increasing the convenience of using the mask shell of the assembled full-face mask.

The foregoing description of the exemplary embodiments of the disclosure has been presented only for the purposes of illustration and description and is not intended to be exhaustive or to limit the disclosure to the precise forms disclosed. Many modifications and variations are possible in light of the above teaching.

The embodiments were chosen and described in order to explain the principles of the disclosure and their practical application so as to enable others skilled in the art to utilize the disclosure and various embodiments and with various modifications as are suited to the particular use contemplated. Alternative embodiments will become apparent to those skilled in the art to which the present disclosure pertains without departing from its spirit and scope.

What is claimed is:
1. An assembled full-face mask, comprising:
a goggle including:
a lens frame being in an annular shape and having a top portion, two lateral portions, a bottom portion, and two pivotal portions that are respectively formed on the two lateral portions;
a pivotal seat disposed on the top portion; and
a lens assembled to the lens frame and arranged in a space that is surroundingly defined by the top portion, the two lateral portions, and the bottom portion;
an outer lens including a sheet and a pivotal frame that is connected to the sheet, wherein the pivotal frame is assembled to the pivotal seat, the sheet covers the lens, and the outer lens is rotatable relative to the goggle along a first axis; and
a mask shell including:
two connection rods respectively assembled to the two pivotal portions; and
a shell body connected to the two connection rods, wherein the mask shell is rotatable relative to the goggle along a second axis that is parallel to and spaced apart from the first axis;
wherein, when one of the outer lens and the mask shell is rotated relative to the goggle by a first angle, another one of the outer lens and the mask shell is rotatable relative to the goggle by a second angle that is less than the first angle;

wherein the pivotal frame includes a rotation shaft arranged along the first axis and two connection bridges that are connected to the rotation shaft and the sheet, a shaft projection area defined by orthogonally projecting the rotation shaft onto the top portion is located at a center region of the top portion, and the rotation shaft includes:
two circular segments rotatably assembled to the pivotal seat; and
a non-circular segment arranged between the two circular segments, wherein the non-circular segment abuts against and is retained by the pivotal seat so as to fix the outer lens at different positions when the outer lens is rotated relative to the goggle.

2. The assembled full-face mask according to claim 1, wherein the pivotal seat includes:
a carrier assembled to the top portion;
two buckling portions connected to the carrier, wherein the two circular segments are respectively buckled into the two buckling portions; and
a limiting cantilever connected to the carrier, wherein the non-circular segment abuts against and is retained by the limiting cantilever, so that the limiting cantilever is configured to provide a reaction force to the non-circular segment.

3. The assembled full-face mask according to claim 1, further defining a bisecting plane perpendicular to the first axis and the second axis, wherein on the bisecting plane, the first axis and the second axis are spaced apart from each other along a first direction by a longitudinal distance, and wherein a lens projection area defined by orthogonally projecting the lens onto the bisecting plane has a height in the first direction, and the longitudinal distance is 30% to 40% of the height.

4. The assembled full-face mask according to claim 3, wherein on the bisecting plane, the first axis and the second axis are spaced apart from each other along a second direction perpendicular to the first direction by a transverse distance, and wherein a frame projection area defined by orthogonally projecting the lens frame onto the bisecting plane has a width in the second direction, and the transverse distance is equal to or less than the width.

5. The assembled full-face mask according to claim 4, wherein a difference between the first angle and the second angle is within a range from 15 degrees to 35 degrees.

6. The assembled full-face mask according to claim 1, wherein the bottom portion is in a substantial W-shape, the two pivotal portions are arranged adjacent to the top portion, and a distance between the second axis and the bottom portion is at least four times of a distance between the second axis and the top portion.

7. The assembled full-face mask according to claim 1, wherein the lens frame includes two positioning columns respectively formed on the two lateral portions, and wherein the two positioning columns respectively abut against and are retained by the two connection rods so as to fix the mask shell at different positions when the mask shell is rotated relative to the goggle.

8. The assembled full-face mask according to claim 7, wherein each of the two connection rods has a plurality of engaging slots, and wherein each of the engaging slots is spaced apart from the second axis by a same distance that is equal to a distance between the second axis and a corresponding one of the two positioning columns, so that any one of the two positioning columns is selectively engaged with one of the engaging slots of a corresponding one of the two connection rods.

9. The assembled full-face mask according to claim 8, wherein, in any one of the two connection rods, the engaging slots jointly define a central angle by taking the second axis as a center of circle, and the central angle is within a range from 45 degrees to 70 degrees.

10. The assembled full-face mask according to claim 1, wherein a top edge of the shell body and a bottom edge of the sheet correspond in shape to each other and are spaced apart from each other so as to form an elongated gap therebetween.

11. The assembled full-face mask according to claim 1, wherein a top edge of the shell body and a bottom edge of the sheet is in contact with an outer surface of the bottom portion of the lens frame.

12. The assembled full-face mask according to claim 1, wherein the pivotal seat is detachably assembled to a center region of the top portion, and each of the two connection rods is detachably assembled to a corresponding one of the two pivotal portions.

13. An assembled full-face mask, comprising:
a goggle;
an outer lens including a sheet and a pivotal frame that is connected to the sheet, wherein the pivotal frame is assembled to the goggle, and the outer lens is rotatable relative to the goggle along a first axis; and
a mask shell including:
two connection rods assembled to the goggle; and
a shell body connected to the two connection rods, wherein the mask shell is rotatable relative to the goggle along a second axis that is parallel to and spaced apart from the first axis;
wherein, when one of the outer lens and the mask shell is rotated relative to the goggle by a first angle, another one of the outer lens and the mask shell is rotatable relative to the goggle by a second angle that is less than the first angle;
wherein the goggle includes two positioning columns, and wherein the two positioning columns respectively abut against and are retained by the two connection rods so as to fix the mask shell at different positions when the mask shell is rotated relative to the goggle;
wherein each of the two connection rods has a plurality of engaging slots, and wherein each of the engaging slots is spaced apart from the second axis by a same distance that is equal to a distance between the second axis and a corresponding one of the two positioning columns, so that any one of the two positioning columns is selectively engaged with one of the engaging slots of a corresponding one of the two connection rods.

14. The assembled full-face mask according to claim 13, wherein a top edge of the shell body and a bottom edge of the sheet correspond in shape to each other and are spaced apart from each other so as to form an elongated gap therebetween, and the top edge of the shell body and the bottom edge of the sheet are in contact with an outer surface of the bottom portion of the goggle.

15. The assembled full-face mask according to claim 13, wherein a difference between the first angle and the second angle is within a range from 15 degrees to 35 degrees.

16. The assembled full-face mask according to claim 13, wherein in any one of the two connection rods, the engaging slots jointly define a central angle by taking the second axis as a center of circle, and the central angle is within a range from 45 degrees to 70 degrees.

17. An assembled full-face mask, comprising:
a goggle including:
- a lens frame being in an annular shape and having a top portion, two lateral portions, a bottom portion, and two pivotal portions that are respectively formed on the two lateral portions;
- a pivotal seat disposed on the top portion; and
- a lens assembled to the lens frame and arranged in a space that is surroundingly defined by the top portion, the two lateral portions, and the bottom portion;

an outer lens including a sheet and a pivotal frame that is connected to the sheet, wherein the pivotal frame is assembled to the pivotal seat, the sheet covers the lens, and the outer lens is rotatable relative to the goggle along a first axis; and a mask shell including:
- two connection rods respectively assembled to the two pivotal portions; and
- a shell body connected to the two connection rods, wherein the mask shell is rotatable relative to the goggle along a second axis that is parallel to and spaced apart from the first axis;

wherein, when one of the outer lens and the mask shell is rotated relative to the goggle by a first angle, another one of the outer lens and the mask shell is rotatable relative to the goggle by a second angle that is less than the first angle;

wherein the pivotal frame includes a rotation shaft arranged along the first axis and two connection bridges that are connected to the rotation shaft and the sheet, and the rotation shaft includes:
- two circular segments rotatably assembled to the pivotal seat; and
- a non-circular segment arranged between the two circular segments, wherein the non-circular segment abuts against and is retained by the pivotal seat so as to fix the outer lens at different positions when the outer lens is rotated relative to the goggle;

wherein the pivotal seat includes:
- a carrier assembled to the top portion;
- two buckling portions connected to the carrier, wherein the two circular segments are respectively buckled into the two buckling portions; and
- a limiting cantilever connected to the carrier, wherein the non-circular segment abuts against and is retained by the limiting cantilever, so that the limiting cantilever is configured to provide a reaction force to the non-circular segment.

* * * * *